(12) United States Patent
Gibbons et al.

(10) Patent No.: US 9,778,242 B2
(45) Date of Patent: Oct. 3, 2017

(54) METAL WORKING FLUID COMPOSITION AND METHOD OF DETECTING FLUID DETERIORATION

(71) Applicant: ILLINOIS TOOL WORKS, INC., Glenview, IL (US)

(72) Inventors: Emily J. Gibbons, Chicago, IL (US); Steven M. Badger, II, Eldridge, IA (US); Leroy N. Hitchcock, Taylor Ridge, IL (US); Jacob F. Harkey, Davenport, IA (US)

(73) Assignee: ILLINOIS TOOL WORKS INC., Glenview, IL (US)

( * ) Notice: Subject to any disclaimer, the term of this patent is extended or adjusted under 35 U.S.C. 154(b) by 62 days.

(21) Appl. No.: 14/466,320

(22) Filed: Aug. 22, 2014

(65) Prior Publication Data

US 2015/0064741 A1 Mar. 5, 2015

Related U.S. Application Data

(60) Provisional application No. 61/872,147, filed on Aug. 30, 2013.

(51) Int. Cl.
*C10M 171/00* (2006.01)
*C10M 173/00* (2006.01)
*G01N 33/28* (2006.01)

(52) U.S. Cl.
CPC ....... *G01N 33/2888* (2013.01); *C10M 171/00* (2013.01); *C10M 171/007* (2013.01);
(Continued)

(58) Field of Classification Search
CPC ............. C10M 135/36; C10M 171/00; C10M 173/00; C10M 171/007; C10N 2230/20;
(Continued)

(56) References Cited

U.S. PATENT DOCUMENTS 2,826,060 A 3/1958 Gordon
2,963,391 A 12/1960 Kubie
(Continued)

FOREIGN PATENT DOCUMENTS

CN 2001007709 Y 1/2008
JP 55076950 A 6/1980
(Continued)

OTHER PUBLICATIONS

Material Safety Data Sheet, Thymol blue, sodium salt MSDS; contact information Sciencelab.com, 14025 Smith Road, Houston, Texas 77396.
(Continued)

*Primary Examiner* — James Goloboy
(74) *Attorney, Agent, or Firm* — Avery N. Goldstein; Blue Filament Law PLLC

(57) ABSTRACT

A wear-indicating metalworking fluid is provided that includes a lubricant base; and a wear-indicating agent. A method of determining wear in a metalworking fluid includes providing wear-indicating metalworking fluid that contains a lubricant base and a wear indicating agent; and observing the visual appearance of the metalworking fluid. A change in visual appearance of the metalworking fluid when compared to an unused metalworking fluid indicates wear of the metalworking fluid.

6 Claims, 1 Drawing Sheet
(1 of 1 Drawing Sheet(s) Filed in Color)

(52) U.S. Cl.
CPC ....... *C10M 173/00* (2013.01); *C10N 2230/20* (2013.01); *C10N 2240/40* (2013.01); *C10N 2240/406* (2013.01); *C10N 2240/407* (2013.01); *C10N 2240/408* (2013.01); *C10N 2240/56* (2013.01)

(58) Field of Classification Search
CPC .......... C10N 2240/40; C10N 2240/406; C10N 2240/407; C10N 2240/408; C10N 2240/56; G01N 33/2888
USPC .................................................. 508/201, 110
See application file for complete search history.

(56) References Cited

U.S. PATENT DOCUMENTS

| | | | |
|---|---|---|---|
| 3,420,779 | A | 1/1969 | Emblem et al. |
| 3,756,949 | A | 9/1973 | Schreurs |
| 4,313,837 | A * | 2/1982 | Vukasovich ......... C10M 173/02 252/387 |
| 2006/0135374 | A1 * | 6/2006 | Cooper .............. C10M 169/044 508/150 |
| 2011/0020940 | A1 * | 1/2011 | Knapton ................ C10L 1/003 436/60 |

FOREIGN PATENT DOCUMENTS

| | | |
|---|---|---|
| JP | 58062559 | 4/1983 |
| JP | 1046649 | 2/1989 |

OTHER PUBLICATIONS

Material Safety Data Sheet, Neutral red MSDS; contact information Sciencelab.com, Inc., 14025 Smith Road, Houston, Texas 77396.
Material Safety Data Sheet, Cresol red MSDS; contact information Sciencelab.com, Inc., 14025 Smith Road, Houston, Texas 77396.
Material Safety Data Sheet, Cresol red, sodium salt MSDS; contact information Sciencelab.com, Inc., 14025 Smith Road, Houston, Texas 77396.
Material Safety Data Sheet, Bromothymol blue MSDS; contact information Sciencelab.com, Inc., 14025 Smith Road, Houston, Texas 77396; pp. 1-5.
Material Safety Data Sheet, product name: α-Naphtholphthalein; Company: Sigma-Aldrich, 3050 Spruce Street, Saint Louis, Missouri 63103, contact information sigma-aldrich.com; print date Jul. 30, 2012; revision date Feb. 28, 2010; 6 pages.

* cited by examiner

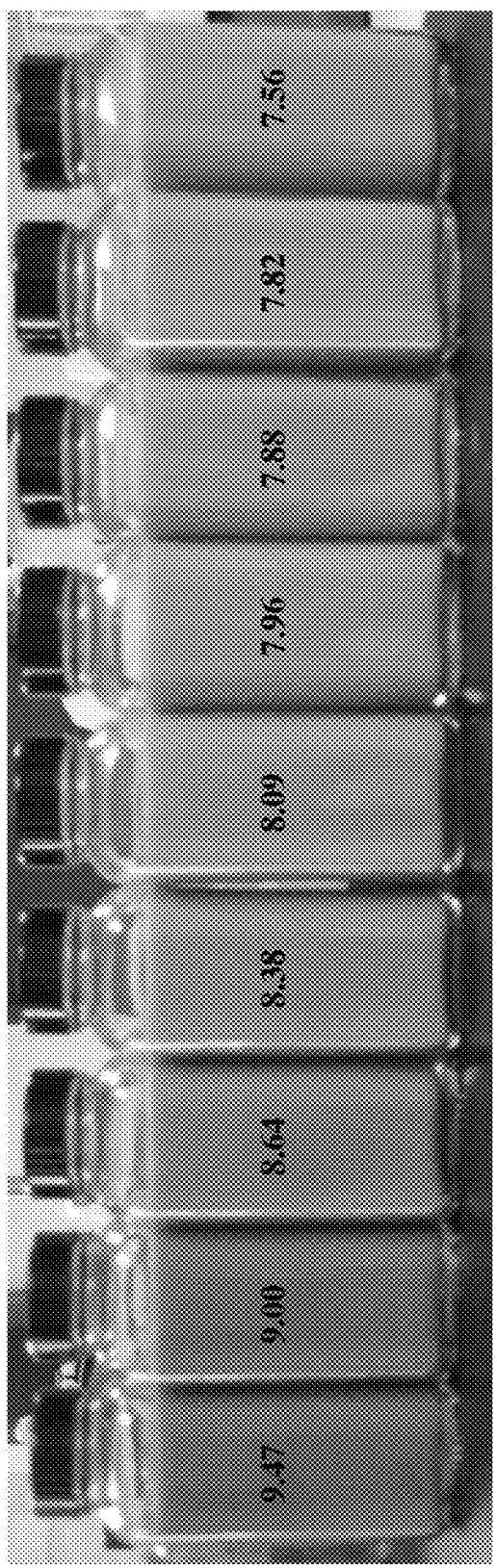

METAL WORKING FLUID COMPOSITION AND METHOD OF DETECTING FLUID DETERIORATION

RELATED APPLICATIONS

This application is a non-provisional application that claims priority benefit of U.S. Provisional application Ser. No. 61/872,147 filed 30 Aug. 2013; the contents of which are hereby incorporated by reference.

FIELD OF THE INVENTION

The present disclosure relates to metalworking fluids (MWF), specifically to metalworking fluid comprising an efficacy indicator.

BACKGROUND OF THE INVENTION

Metalworking fluids include a range of engineered oils and other liquids that are used to optimize the metalworking process. Typically, metalworking fluids (MWF) are used to aid the cutting, grinding, or forming of metal and to provide good finish and workpiece quality while extending the life of the machine tools. The fluids cool and lubricate the metal-tool interface while aiding in the removal of fine particles or chips of metal away from the work-piece. The fluid can also provide adequate temporary indoor rust protection to the workpiece while in-process or prior to assembly. Water-based fluids can be configured to resist the growth of microorganisms and/or the development of objectionable odors.

While it is widely acknowledged that a well thought-out and consistently enforced fluid management plan is the best way to maintain stability in a metalworking fluid system, however, this has proven challenging. The primary reasons behind poor maintenance are, among others, a lack of understanding on the part of the individuals tasked with this responsibility, the complexity of the factors involved, and the time required to perform the recommended testing procedures on a regular basis, in other words, proper quality control and assurance (QC/QA).

Several attempts were made to overcome these problems. The solutions proposed were to develop fluids that are more resistant to chemical degradation by external factors. This resulted in a generation of metalworking fluids that are much more expensive than previous formulas due in part to a sharp increase in the strength and quantity of antimicrobials used in the fluids and increasing use of synergists in combination with antimicrobials.

Continuing regulatory pressures on metalworking fluids in general, and antimicrobial pesticides in particular, combined with the higher costs needed to ensure they are validated for commercial use, point to the fact that fewer active antimicrobial ingredients will be available in the future. For example, the EPA's Office of Pesticide Programs (OPP) is currently considering imposing rigorous new requirements on the leading microbicide used in metalworking fluids which, if passed, would effectively remove the biocide from the U.S. metalworking fluid market.

Accordingly, there remains a need for an improved metalworking fluid capable of indicating deterioration and loss of efficacy. Additionally, there is a need for an environmentally friendly metalworking fluid.

SUMMARY OF THE INVENTION

Disclosed, in various embodiments, are metalworking fluids, specifically metalworking fluids comprising an efficacy indicator.

In one inventive embodiment, wear-indicating metalworking fluid, is provided that includes a lubricant base; and a wear-indicating agent.

In another inventive embodiment, provided herein is a method of determining wear in a metalworking fluid, that includes providing wear-indicating metalworking fluid, comprising a lubricant base and a wear indicating agent; and observing the visual appearance of the metalworking fluid, whereby change in visual appearance of the metalworking fluid when compared to an unused metalworking fluid indicates wear of the metalworking fluid.

In yet another inventive embodiment, provided herein is a kit for indicating wear of a metalworking fluid, that includes a wear-indicating agent, packaging; and instructions.

These and other features of the metalworking fluids include an efficacy indicator that will become apparent from the following detailed description when read in conjunction with the figures and examples, which are exemplary, not limiting of the appended claims.

BRIEF DESCRIPTION OF THE FIGURES

The patent or application file contains at least one drawing executed in color. Copies of this patent or patent application publication with color drawing(s) will be provided by the Office upon request and payment of the necessary fee.

For a better understanding of the metalworking fluids comprising an efficacy indicator, with regard to the embodiments thereof, reference is made to the accompanying examples and FIGURE, in which:

FIG. 1 shows the effect of pH change on the indicator color.

DESCRIPTION OF THE INVENTION

Provided herein are embodiments of metalworking fluids that include an efficacy indicator. The metalworking fluids provided are useful for indicating the metalworking fluid may no longer be effective for its intended purpose.

The effectiveness of a metalworking fluid for heat transfer and lubrication decreases for a number of reasons. These fluids are used in difficult and extreme conditions and will naturally break down over time as a result. Additionally, they accumulate foreign substances including tramp oil, swarf, dissolved minerals, and/or dirt from the process; these substances prevent the fluid from working. Selective depletion of a fluid component can also reduce its effectiveness. For example, swarf is particulate metal created during the grinding or cutting of metals. The presence of swarf creates friction, defeating both the lubricating ability and cooling capabilities of the metalworking fluid. The increased concentration of tramp oil (oil present in a metalworking fluid that is not part of the original concentrate) similarly interferes with fluid performance.

Metalworking fluids, particularly water-dilutable types, are formulated to operate within a certain range of conditions in areas such as concentration, pH, dirt levels, tramp oil, bacteria, and fungus. When fluid conditions fall out of this range, in one or more of these areas, performance problems will develop. Therefore, metalworking fluids require active maintenance on the part of the customer/user to ensure optimum results and longevity. In fact, management of metalworking fluids is the most important step in improving fluid life and reducing occupational hazards associated with metalworking fluids.

Metal metalworking fluids are dynamic systems due to their usage and environment. Because its characteristics are widely changing during time, the same metalworking fluid may have a different composition after use in different systems for any extended period. Therefore, cutting fluid maintenance can be very important for its proper application in processes. In addition, keeping the fluid properties between the proposed tolerances can increase the metalworking fluid's shelf life time and efficacy. Typically different maintenance programs are focused on monitoring wear indicating parameters and proper addition of chemicals in order to keep these parameters between the predetermined limits. Some of the wear-indicating parameters that are monitored in order to keep metalworking fluid ability to perform can be, for example, lubricant (e.g., oil) concentration, pH level, microbial load, and corrosion inhibition.

Oil concentration, or alternatively, lubricant base such as synthetic emulsions (e.g. oil-in-water (O/W) emulsion or water-in-oil-in-water (W/O/W)) of metalworking fluids, is essential for its performance characteristics. Additionally, proper concentration can maximize tool (e.g., on which the metalworking fluid is used) longevity and can also serve as an indicator of microbial growth rate. High concentration can increase fluid costs through wasted lubricant, reduce dissipation of heat, increase foaming, increase lubrication, increases the risk for generating metal accumulation (build-up) on the cutting edge (BUE), thus decreasing the efficacy of the metalworking fluid.

Certain metalworking fluids evaporate under standard temperature and pressure (STP), high oil/lubricant concentration can additionally increase its toxicity. Factors leading to high concentration of oil/lubricant in metalworking fluids can, for example, be water evaporation due to heat generated in machining processes. Conversely, low concentration can cause poor lubricity, shorter tool life, increased biological activity and increased risk of rust formation on contacted metal surfaces. Many chemical and physical processes can influence oil concentration decay, for example, bacterial attack, reaction of oil molecules with elements in water or metal, lubricant adhesion to the metal parts, degradation due to temperature and pressure in the cutting region, reaction with light and aeration etc. A wear indicator can therefore be introduced into the oil or dispersed phase of the lubricant base emulsion of the compositions and kits described herein, whereby upon changes in concentration of the oil/lubricant, or, upon contact with other indicator solubilized in the continuous aqueous phase, (as in the case of emulsions), the indicators can react and produce a color not observed in the unused, fresh metalworking fluid.

Metalworking fluids' pH can be a very good indicator of an effective metalworking fluid. The term pH refers to the concentration of hydrogen ions (pH=−log [$H^+$]). Neutral pH value is 7. Lower values represent acidic solutions while pH values higher than 7.0 represent alkaline solutions. Recommended pH region for water-dilutable metalworking fluids is, for example, 8.0 to 10.0, specifically, 8.2 to 9.8 or 8.4 to 9.6, more specifically, 8.6 to 9.4 or 8.8 to 9.2. At pH values lower than 8.0, the metalworking fluid can lose its efficiency. Likewise corrosion inhibition properties can decrease and microbial contamination can increase. At pH levels equal to or higher than 9.5, the risk for skin irritation and dermatitis can significantly increase.

In an inventive embodiment, a color-changing component can be added to water-dilutable metalworking fluid compositions and kits described herein. As the pH of the metalworking fluid begins to migrate outside the accepted operating range, possibly indicating bacteria and/or fungal growth or concentration change, the fluid can begin to change color, thus capable of providing the user with a distinct visual indication of the chemical change. At the predetermined operating pH as described herein, the metalworking fluid compositions and kits described herein comprising an efficacy indicator, can be a colored metalworking fluid. As the pH moves outside the accepted operating range, the fluid color changes gradually to other hues and/or Chroma. When the metalworking fluid's pH is well outside the optimal range and maintenance is required, the color of the metalworking fluid will be of a different color altogether. Addition of additives or concentration modification may correct the metalworking fluid's pH, causing the fluid to return it to its original color.

Microbial contamination of a cutting fluid can be additionally estimated by indicating dissolved oxygen in the metalworking fluid. At STP a circulated fluid can dissolve about 9 ppm oxygen when it is exposed to the air. Since the oxygen is necessary for aerobic bacteria growing, by measuring the dissolved oxygen good estimation of biological contamination can be obtained. In some inventive embodiments, an oxygen-sensitive dye can be incorporated into the metalworking fluid compositions and kits described herein, whereby, upon excessive aeration and dissolution of oxygen in the metalworking fluid, the oxygen sensitive dye can react and provide a visual indication of the wear parameter (e.g., dissolved oxygen as indication of increased risk for microbial growth).

Corrosion inhibition properties of metalworking fluids can be very important for protecting metal parts that are in contact with the metalworking fluid. In addition, since the corrosion protection of metalworking fluids can decrease significantly when oil concentration is low enough to completely dissolve the oil in water, oil concentration can serve as a wear indicator for adding oil into the system upon loss of corrosion inhibition properties.

In other inventive embodiments, provided herein is a wear-indicating metalworking fluid (MWF), that includes a lubricant base; and a wear-indicating agent. The wear-indicating agent can be combined with the lubricant base or, for example with a coolant, a washing compound, water-based corrosion inhibitor, a cutting fluid or other water-dilutable MWF.

The term "water-dilutable" refers to circumstances wherein the metalworking fluid, when diluted with water, forms a homogeneous phase with the water and the so called phase inversion peak preferably is absent upon dilution or is at least, very small. Accordingly, the kinematic viscosity of the metalworking fluid disclosed herein never exceeds the kinematic viscosity of 100% metalworking fluid upon dilution with water, measured in $mm^2 \cdot s^{-1}$ of the resistance to flow of a fluid under gravity, determined by ASTM D445-06.

pH and by implication alkalinity can have an effect on many different metalworking fluid characteristics. These characteristics include, for example, corrosion, metal solubility, emulsion stability, skin toxicity, bacterial and fungal growth, or machine tool compatibility and their combination.

For example, ferrous metals can be protected from corrosion by a higher pH. Ferrous materials are less likely to have corrosion the closer the pH is to 14. White and yellow metals tend to be amphoteric. In other words, as the pH is raised or lowered from 7.0, the probability of corrosion increases. Likewise, solubility of metals into MWFs is similar to corrosion, except that the amount of metal that can be put into solution is strongly influenced by the amount of reserve alkalinity (in other words, the amount of a specific acid that is necessary to suppress the pH to 4.5), while maintaining pH at the appropriate levels for the specific metalworking fluid. Accordingly, pH indicators specific for each of the predetermined pH ranges can be used as indicators for loss of corrosion inhibition properties resulting from wear of the MWF.

As for emulsion stability of emulsion comprising soluble oils, changes in pH indicate changes in the ionic strength of the MWF, which in turn can affect dispersed phase particle size, thereby affecting processes such as separation (coalescence) and viscosity. Tighter emulsions (in other words, emulsions with smaller dispersed phase particle size), wet better, and have lower carryoff; those that are more course (in other words, emulsions with larger dispersed phase particle size), can provide better hydrodynamic (mechanical) lubricity and much more carryoff. Likewise, depending on the nature of the tramp oil, changes in pH can either reject tramp oil or emulsify it. Accordingly, pH indicators specific for each of the predetermined pH ranges can be used as indicators for changes in emulsion stability resulting from wear of the MWF, leading to changes in viscosity.

Toxicity—the farther the pH of a working solution moves from 7.0, the more likely it is for contact dermatitis to result. Typically, a working pH of less than 10.5 is well tolerated. When skin is exposed to alkaline pH, the alkalinity in the fluid can "saponify" the oil in the skin causing it to dry out ("dish pan" hands) and even crack. Accordingly, pH indicators specific for each of the predetermined pH ranges can be used as indicators for changes in emulsion stability resulting from wear of the MWF, leading to changes in toxicity.

Although bacteria and fungus can grow at any pH and in nearly any situation, the growth rate of bacteria typically present in metalworking fluids is reduced as the pH is increased. So, circumstances in which the pH of a cutting fluid during usage is decreased can indicate increased risk for bacterial growth.

As for machine tool compatibility; extremes of pH, either very alkaline or acidic, can cause machine tool maintenance problems, such as corrosion, where different materials meet (as when aluminum and/or brass are attached or in contact with steel or cast iron). At either pH extreme, elastomers (e.g., seals and O-rings) tend to lose their flexibility and plastic "glazing" can become quite brittle. Accordingly, pH indicators specific for each of the predetermined pH ranges can be used as indicators for changes in machine compatibility resulting from wear of the MWF.

In an inventive embodiment, the wear indicating agent used in the compositions, kits and methods described herein is carmine, carminic acid, curry powder, thymol blue, pentamethoxy red, tropaeolin O, tropaeolin OO, tropaeolin OOO, 2,4-dinitrophenol, methyl yellow, methyl orange, bromophenol blue, tetrabromophenol blue, alizarin sodium sulfonate, alpha-naphthyl red, para-ethoxychrysoidine, bromocresol green, methyl red, bromocresol purple, chlorophenol red, bromothymol blue, para-nitrophenol, azolitmin, phenol red, neutral red, rosolic acid, cresol red, naphtholphthalein, phenolphthalein, naphtholbenzein, thymolphthalein, nile blue, alizarin yellow, salicyl yellow, diazo violet, nitramine, poirrier's blue, trinitrobenzoic acid, extracts from: beets, blackberries, blueberries, carrots, cherries, delphinium petals, geranium petals, grapes, grape seeds, horse chestnut leaves, morning glories, pansy petals, petunia petals, primrose, poppy petals, purple peonies, red radish, red cabbage, rhubarb, rose petals, strawberries, tea, turmeric, tulip petals, thyme, violet petals, vanilla, a thermosensitive dye, an oxygen sensitive dye, or a combination comprising at least one of the foregoing.

The chemical wear-indicating agent used in the compositions, kits and methods described herein, can for example, change color in response to a change in a wear-indicating parameter of the metalworking fluid, such as, for example, change in pH, change in concentration of a component of the metalworking fluid, viscosity, conductivity, bacterial or fungal growth, loss of corrosion protection, change in oil or additive content, loss of lubricity, or a combination comprising at least one of the foregoing. Upon change of a wear-indicating parameter of the metalworking fluid used in the compositions, kits and methods described herein, above a predetermined level, the visual appearance of the metalworking fluid alters and also, upon return of the wear-indicating parameter of the metalworking fluid to the predetermined level, the visual appearance of the metalworking fluid is restored.

The indicators used in the compositions, methods and kits provided herein, can be further optimized to provide the desired degree of change as measured using the Hunter L,a,b color space. In the Hunter color space L value changes from 0-100 providing the value for the change in lightness between a perfectly transparent diffuser (L=100) and completely dark, opaque matter (L=0). 'a and 'b axis have no specific numerical limits and their value reflect the change between green (negative) and red (positive) for the a axis; and between blue (negative) and yellow (positive for the 'b axis.

Accordingly, the determination of whether the MWF should be treated could be done upon an observed change in Lab values of beyond a predetermined level for each of the parameters, whereby each parameter can indicate that different wear-indicating parameter (e.g. rust inhibition, machine compatibility, toxicity, etc.) has migrated out of the MWF operational limits. For example, a positive change larger than 0.1 on the 'a' scale can indicate loss of rust inhibition with other Lab parameters remaining within tolerance levels would prompt a treatment of the MWF to return the color to the Lab levels thus recovering the MWF rust inhibiting properties. Likewise, negative change in 'L value may indicate emulsion stability issues that would potentially be treated differently than the rust inhibition recovery treatment.

The compositions, kits and methods described herein can further includes metal deactivators (e.g., a tolytriazole derivative and the like), corrosion inhibitors (e.g. monoisopropanolamine, diisopropanolamine, Gateway CP-105, benzotriazol, tolytriazol, sebacic acid, Corfree M1, Irgacor 190 plus, and derivatives thereof, and the like), an antimicrobial agent (e.g., o-phenylphenol, morpholine, and the like), extreme pressure agents (e.g., chlorinated paraffins, chlorinated waxes, chlorinated esters, chlorinated fatty acids; sulfurized fats; sulfurized olefins; polysulfides; sulfur-chlorinated compounds; sulfurized sulfonates; phosphate esters; phosphate fatty acids; phosphate amines, and combinations thereof), an antifriction agent (e.g., soybean oil, canola oil, sunflower oil, jatropha oil, palm oil, neopentyl glycol dioleate, trimethylolpropane trioleate, pentaerythritol tetraoleate, propylene glycol dioleate, ricinoleic acid condensate, and methyl ester of soybean oil, canola oil, jatropha oil or palm oil, and combinations thereof; polymeric substances (e.g., polyethylene glycols, acrylic acids, polyvinylpyrolidones, and the like); bactericides (e.g., thiazoline, pyridine, morpholine, phenol, nitro- and IPBC-based preservatives, and the like); antioxidants; chelating agents (e.g. ethylenediaminetetraacetic acid (EDTA), diethylenetriaminepentaacetic acid (DTPA), nitrilotriacetic acid (NTA), iminodiacetic acid (IDA), iminotriacetic acid (ITA), ethylenediamine (En), N,N'-diethylenediamine (Den), diethylenetriamine (DTN), diethylenetetramine (Trien), triaminotriethylene amine, propylenediamine, glycolic acid, hydroxybutyric acid, salicylic acid, benzoic acid, mixtures thereof); pH regulators (e.g., monoethanolamine, diethanolamine, triethanolamine, monoisopropanolamine, diisopropanolamine, triisopropanolamine, aminomethyl propanol, diglycolamine, and the like), or a combination thereof.

In an embodiment, the kits and compositions described can be used in the methods provided. Accordingly, provided is a method of determining wear in a metalworking fluid, comprising the step of providing wear-indicating metalworking fluid, comprising a lubricant base and a wear indicating agent; and observing the visual appearance of the metalworking fluid, whereby change in visual appearance of the metalworking fluid when compared to an unused metalworking fluid indicates wear of the metalworking fluid.

The present disclosure is now illustrated by reference to the following example. Unless otherwise specified, all parts, percentages and ratios are on a weight basis.

EXAMPLES

Procedure

One way to determine the health of MWF is by tracking the fluid's pH. The pH of MWF that is performing well is 8.0-10.0. A MWF that is beginning to fail has pH value that is equal to or less than 8.0. A series of pH indicators (VWR Scientific), which change color in the range of pH values of 6.0-9.0 were obtained and are listed in the Table below:

TABLE 1

Indicators' pH ranges

| Indicator | pH range | Color Change (Acid → Base) | CAS # |
|---|---|---|---|
| Bromothymol Blue | 6.0→7.0 | Yellow → Blue | 46-59-5 |
| Cresol Red sodium salt | 7.0→8.0 | Yellow → Red | 62625-29-0 |
| Neutral Red | 6.8→8.0 | Red → Amber | 553-24-2 |
| α-Naphtholphthalein | 7.3→8.7 | Rose → Green | 596-01-0 |
| Cresol red | 7.0→8.8 | Yellow → Red | 1733-12-6 |
| Thymol Blue sodium salt | 8.0→9.6 | Yellow → Blue | 62625-21-2 |

0.04% (w/w indicator/MWF), were added to a sample of Rustlick Ultracut Pro CF (water-soluble oil with maximum biostability specifically formulated for heavy-duty applications of ferrous/nonferrous metals, aluminum, brass bronze, and copper) and the compatibility of each indicator with the MWF was determined. Results are shown in Table 2.

TABLE 2

Base/Indicator Samples

| Ex # | Material | W (ml's)* | Indicator Soluble? | Appearance |
|---|---|---|---|---|
| Ex. 1 | UlltraCut Pro CF Bromothymol Blue | 200.01 0.0810 | Yes | Blue → Blue/Green |
| Ex. 2 | UlltraCut Pro CF Cresol red | 200.07 0.079 | Yes | Red → Wine |
| Ex. 3 | UlltraCut Pro CF Neutral Red | 200.00 0.0804 | Partially | Dark Amber |
| Ex. 4 | UlltraCut Pro CF α-Naphtholphthalein | 200.02 0.0799 | Yes | Green |

TABLE 2-continued

Base/Indicator Samples

| Ex # | Material | W (ml's)* | Indicator Soluble? | Appearance |
|---|---|---|---|---|
| Ex. 5 | UlltraCut Pro CF Cresol Red sodium salt | 200.06 0.0810 | Yes | Red Wine |
| Ex. 6 | UlltraCut Pro CF Thymol Blue sodium salt | 200.12 0.0802 | Yes | Dark Amber |

Five of the six indicators are readily soluble in the Ultracut Pro CF. The Neutral Red (CAS#:553-24-2) was partially soluble after two hours of mixing.

The five soluble indicators were then diluted in water at a 10:1 ratio (10 parts water:1 part (MWF+Indicator)). Initial pH was recorded and Phosphoric Acid was added until color changed, upon which, pH was recorded again. Results are shown in Table 3.

| # | Initial Color | Indicator | Initial pH | Final Color | Final pH |
|---|---|---|---|---|---|
| Ex. 1 | Deep milky Blue | Bromothymol Blue | 9.6 | Milky Yellow | 7.47 |
| Ex. 2 | Bright milky purple | Cresol red | 9.56 | Milky yellow | 6.99 |
| Ex. 3 | Skip | Neutral Red | Sample did not fully solubilize (see Table 2) | | |
| Ex. 4 | Milky blue/green | α-Naphtholphthalein | 9.58 | Milky White | 8.33 |
| Ex. 5 | Bright milky purple | Cresol Red sodium salt | 9.48 | Milky yellow | 7.23 |
| Ex. 6 | Dark milky blue/green | Thymol Blue sodium salt | 9.50 | Milky yellow/orange | 8.32 |

Example 1 produced color change at pH value that was too low. Example 2 produced color change at pH values that are too low. The MWF turned red halfway through the color change when the pH value was still appropriate for the purpose of the MWF. An example where change from initial color to red at the proper pH value would be beneficial. Color change in Ex. 4 occurred too son. The MWF is still operational at pH value of 8.33. Ex. 5, performed similar to Ex. 2. The color change in Ex. 6 occurred too soon, In other words, the pH value at which the color change occurred was still within the operational limits of the MWF.

Ex. 1 provided color change at the best range (pH=7.47). In addition, it was determined that change to a red color would be the preferred change (although other colors could also be obtained and give the proper indication).

Neutral Red was determined to be soluble in water. Accordingly, 4 gr Neutral Red were dissolved into 100 ml (4.0% w/w) water at room temperature. To provide both the pH range desired and the color indication needed, Neutral Red solution and Bromothymol Blue were combined with Ultracut Pro CF. Table 4 shows the combination used:

| Ex # | Material | W (ml's)* | Indicator Soluble? | Appearance |
|---|---|---|---|---|
| Ex. 7 | UlltraCut Pro CF Bromothymol Blue Neutral Red Solution (4% w/w) | 197.8900 0.0794 2.0000 | Yes Yes | Dark Green |

Initial pH of the MWF was then recorded and Phosphoric Acid was added until color changed, upon which, pH was recorded again. Results are shown in Table 5:

| # | Initial Color | Indicator | Initial pH | Final Color | Final pH |
|---|---|---|---|---|---|
| Ex. 7 | Milky Blue/Green | Bromothymol Blue/ Neutral Red Solution (4% w/w) | 9.58 | Milky Pink | 8.05 |

As shown in Ex. 7, the combination of indicators changes color at the correct pH, where the MWF changes from milky blue/green to milky pink.

The color change as a function of pH was evaluated. 90 g. of water and 10 g. of Ex. 7 were placed in nine 4 oz. glass jars. Jars were capped in hand mixed. 0-8 drops of phosphoric acid (75%) were dosed into each jar, whereupon mixing the color change and resulting pH were recorded. Results of the effect of pH on color are shown in Table 6.

TABLE 6

| Jar | 1 | 2 | 3 | 4 | 5 | 6 | 7 | 8 | 9 |
|---|---|---|---|---|---|---|---|---|---|
| Drops $H_3PO_4$ | 0 | 1 | 2 | 3 | 4 | 5 | 6 | 7 | 8 |
| Color | Blue/ Green | Blue/ Green | Blue/ Green | Blue/ Green | Gray | Pink | Pink | Pink | Pink |
| pH | 9.58 | 9.16 | 8.84 | 8.52 | 8.32 | 8.05 | 7.95 | 7.82 | 7.68 |

To provide earlier warning, the indicator combination was changed to obtain darker red at higher pH values (pH=8.5) by changing the concentration of the indicators used. The composition is shown in Table 7.

TABLE 7

Composition of Ex. 8

| Ex # | Material | W (ml's)* | Indicator Soluble? | Appearance |
|---|---|---|---|---|
| Ex. 8 | UIltraCut Pro CF | 196.0100 | | Dark Green |
| | Bromothymol Blue | 0.0799 | Yes | |
| | Neutral Red Solution (4% w/w) | 4.0200 | Yes | |

Using the same procedure as in Ex. 7, 0-8 drops of phosphoric acid (75%) were dosed into each jar, whereupon (hand) mixing the color change and resulting pH were recorded. Results of the effect of pH on color are shown in Table 8 and FIG. 1.

TABLE 8

Effect of drop number on color and pH in Ex. 8

| Jar | 1 | 2 | 3 | 4 | 5 | 6 | 7 | 8 | 9 |
|---|---|---|---|---|---|---|---|---|---|
| Drops $H_3PO_4$ | 0 | 1 | 2 | 3 | 4 | 5 | 6 | 7 | 8 |
| Color | Dark Blue/ Green | Light Blue/ Green | Gray/ Green | Gray/ Pink | Pink | Pink | Pink | Pink | Pink |
| pH | 9.47 | 9.00 | 8.64 | 8.38 | 8.09 | 7.96 | 7.88 | 7.82 | 7.56 |

As indicated in Table 8 and shown in FIG. 1, the pink color starts appearing at pH values of 8.38. Moreover, the pink color is more intense.

All ranges disclosed herein are inclusive of the endpoints, and the endpoints are independently combinable with each other. It is to be understood that in instances where a range of values are provided that the range is intended to encompass not only the end point values of the range but also intermediate values of the range as explicitly being included within the range and varying by the last significant figure of the range. By way of example, a recited range of from 1 to 4 is intended to include 1-2, 1-3, 2-4, 3-4, and 1-4.

"Combination" is inclusive of blends, mixtures, alloys, reaction products, and the like. The terms "a", "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, when present, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

While particular embodiments have been described, alternatives, modifications, variations, improvements, and substantial equivalents that are or may be presently unforeseen may arise to applicants or others skilled in the art. Accordingly, the appended claims as filed and as they may be amended, are intended to embrace all such alternatives, modifications variations, improvements, and substantial equivalents.

The invention claimed is:

1. A wear-indicating metalworking fluid, comprising:
    a lubricant base in a continuous aqueous phase and having an initial pH; and
    a first wear-indicating agent dissolved in the lubricant base, the wear-indicating agent changing to a first wear-indicating agent color in response to a change in pH and is colormetrically reversible when the pH is restored to the initial pH; and
    a second wear-indicating agent dissolved in the lubricant base, the second wear-indicating agent changing to a second wear-indicating agent color in response to a change in the pH, the second wear-indicating agent color being different than the first wear-indicating agent color and at a different value in the pH relative to the first wear-indicating agent;

wherein the lubricant base and the first and second wear-indicating agents collectively define a fluid color, the first and second wear-indicating agents acting as an efficacy indicator when the pH is in an acceptable operating range with an initial color for the fluid color, and as the pH moves below the accepted operating range of the pH, the fluid color changes from the initial color to other hues when the pH is between 9.00 and 8.32 wherein the fluid color change from the initial color to other hues is due to the color changes of the first wear-indicating agent and when the pH is between about 7.56 and about 8.09 for the metalworking fluid the fluid color is a terminal color, the terminal color is associated with the color changes of the second wear indicating agent and the terminal color is different than the initial color and is also different than the other hues associated with the color changes of the first wear-indicating agent.

2. The fluid of claim 1 wherein the first and second wear indicating agents are each independently selected from the group consisting of: curry powder, thymol blue, pentamethoxy red, tropaeolin OOO, tetrabromophenol blue, bromothymol blue, para-nitrophenol, azolitmin, phenol red, neutral red, cresol red, naphtholphthalein, phenolphthalein, naphtholbenzein, extracts from: blackberries, carrots, cherries, delphinium petals, geranium petals, grapes, grape seeds, horse chestnut leaves, morning glories, pansy petals, petunia petals, primrose, poppy petals, purple peonies, red radish, red cabbage, rhubarb, rose petals, strawberries, tea, turmeric, tulip petals, thyme, violet petals, and vanilla.

3. The fluid of claim 1 wherein upon return of the pH of the metalworking fluid to the initial pH, the visual appearance of the metalworking fluid is restored.

4. The fluid of claim 1 further comprising at least one of: a metal deactivator, a corrosion inhibitor, an antimicrobial agent, an extreme pressure agent, an antifriction agent, a bactericide, an antioxidant, a chelating agent, a pH buffer.

5. A method of determining wear in a metalworking fluid, comprising:
providing wear-indicating metalworking fluid, comprising a lubricant base in a continuous aqueous phase and having an initial pH and a first wear indicating agent dissolved in the lubricant base, the wear-indicating agent changing to a first wear-indicating agent color in response to a change in pH and is colormetrically reversible when the pH is restored to the initial pH; and
providing a second wear-indicating agent dissolved in the lubricant base, the second wear-indicating agent changing to a second wear-indicating agent color in response to a change in the pH, the second wear-indicating agent color being different than the first wear-indicating agent color and at a different value in the pH relative to the first wear-indicating agent;
observing the visual appearance of the metalworking fluid over time, whereby change in visual appearance of the metalworking fluid when compared to an unused metalworking fluid indicates wear of the metalworking fluid; and
wherein the lubricant base and the first and second wear-indicating agents collectively define a fluid color, the first and second wear-indicating agents acting as an efficacy indicator when the pH is in an acceptable operating range with an initial color for the fluid color, and as the pH moves below the accepted operating range of the pH, the fluid color changes from the initial color to other hues when the pH is between 9.00 and 8.32 wherein the fluid color change from the initial color to other hues is due to the color changes of the first wear-indicating agent and when the pH is between about 7.56 and about 8.09 for the metalworking fluid the fluid color is a terminal color, the terminal color is associated with the color changes of the second wear indicating agent and the terminal color is different than the initial color and is also different than the other hues associated with the color changes of the first wear-indicating agent.

6. The fluid of claim 5 wherein the first and second wear indicating agents are each independently selected from the group consisting of: curry powder, thymol blue, pentamethoxy red, tropaeolin OOO, tetrabromophenol blue, bromothymol blue, para-nitrophenol, azolitmin, phenol red, neutral red, cresol red, naphtholphthalein, phenolphthalein, naphtholbenzein, extracts from: blackberries, carrots, cherries, delphinium petals, geranium petals, grapes, grape seeds, horse chestnut leaves, morning glories, pansy petals, petunia petals, primrose, poppy petals, purple peonies, red radish, red cabbage, rhubarb, rose petals, strawberries, tea, turmeric, tulip petals, thyme, violet petals, and vanilla.

* * * * *